US008246833B2

(12) United States Patent
Eriksson et al.

(10) Patent No.: US 8,246,833 B2
(45) Date of Patent: Aug. 21, 2012

(54) CHROMATOGRAPHY COLUMN AND MAINTENANCE METHOD

(75) Inventors: Stefan Kjell Eriksson, Uppsala (SE); John Davis, Singapore (SG); Mats O. Hansson, Uppsala (SE); Kyril Dambuleff, Frenchtown, NJ (US); Roger Nordberg, Uppsala (SE)

(73) Assignee: GE Healthcare Bio-Sciences AB, Uppsala (SE)

( * ) Notice: Subject to any disclaimer, the term of this patent is extended or adjusted under 35 U.S.C. 154(b) by 382 days.

(21) Appl. No.: 12/640,193

(22) Filed: Dec. 17, 2009

(65) Prior Publication Data

US 2011/0147311 A1 Jun. 23, 2011

(51) Int. Cl.
*B01D 15/08* (2006.01)
(52) U.S. Cl. ..................... 210/656; 210/198.2
(58) Field of Classification Search .......... 210/635, 210/656, 659, 198.2; 95/82; 96/101
See application file for complete search history.

(56) References Cited

U.S. PATENT DOCUMENTS

| | | | | |
|---|---|---|---|---|
| 5,167,809 A | * | 12/1992 | Mann et al. | 210/198.2 |
| 6,001,260 A | * | 12/1999 | Hatch et al. | 210/656 |
| 6,190,560 B1 | | 2/2001 | Mann | |
| 6,736,974 B1 | | 5/2004 | Mann | |
| 7,041,216 B2 | * | 5/2006 | Dunkley et al. | 210/198.2 |
| 7,604,747 B2 | * | 10/2009 | Spencer et al. | 210/656 |
| 7,708,891 B2 | * | 5/2010 | Davis et al. | 210/656 |
| 7,780,853 B2 | * | 8/2010 | Davis et al. | 210/656 |
| 2008/0308498 A1 | | 12/2008 | Davis et al. | |
| 2009/0078634 A1 | * | 3/2009 | Dunkley et al. | 210/198.2 |

FOREIGN PATENT DOCUMENTS

| | | |
|---|---|---|
| WO | WO 2005/056156 | 6/2005 |
| WO | WO 2009/093952 | 7/2009 |

* cited by examiner

*Primary Examiner* — Ernest G Therkorn

(57) ABSTRACT

A method of maintenance of a chromatography column is described which does not require the use of a hoist or crane for disassembly. The method provides improved operator safety by reducing the need for the operator to work below a suspended or supported load within the column. The provision of guide elements which can be reversibly attached to the column facilitates removal or insertion of column components.

10 Claims, 18 Drawing Sheets

CHROMATOGRAPHY COLUMN AND MAINTENANCE METHOD

FIELD OF THE INVENTION

The present invention relates to chromatography columns and methods for operating columns in industrial-scale chromatography. In particular, the invention is concerned with chromatography columns and safer methods for removing and replacing column components, such as bed supports and/or distributors, in order to perform maintenance or inspection on such columns, without the need for heavy lifting equipment such as hoists or cranes to dismantle the columns.

BACKGROUND OF THE INVENTION

Chromatography columns may be used in industrial processes to purify process liquids and separate substances of interest from process liquids; typical examples include large-scale preparative purification of fine chemicals and pharmaceuticals, together with biological products.

Industrial-scale chromatography columns typically comprise a hollow, axially vertical tubular housing including a liquid inlet at the upper end and through which the buffer and substances to be separated are dispensed to the media bed located within the cavity of the tube, and a liquid collecting system at the lower end for collecting substances and buffer. The particulate chromatographic media or bed through which the buffer fluid and/or substances to be separated and purified percolates is located between the liquid inlet and collecting system.

An adapter assembly is typically affixed to the upper end of the tubular housing and a base assembly to the lower end where it is bolted to the bottom flanges. Each of these assemblies typically comprises a strong backing plate and a distributor which further supports a bed support: a bed support is a layer of mesh, filter, sinter, screen or other fluid-permeable media-retaining material which permits process liquid flow into and out of the chromatography bed space or cavity while retaining the bed of particulate medium. To provide adjustability and control of the bed height and bed compression, the adapter assembly is typically made in the form of a piston or sliding adapter in the column tube interior. After the column is charged with bed media, typically through a nozzle, the adapter may be forced toward the bottom of the tube to compress or pressurize the media bed. Generally the base assembly is a fixed structure which is bolted against the bottom flange of the column tube but, in some instances, may also be in the form of a movably slidable piston or adapter.

The backing plate of the base assembly generally acts as a support for the column, being itself supported on legs or some other stand arrangement which allows clearance for outlet pipe work projecting beneath the base assembly.

When such a column requires maintenance to, cleaning of, or inspection of internal components, such as the valves, seals, bed supports, distribution systems etc., heavy lifting gear such as a crane or hoist is necessary to lift the upper end/adapter assembly away from the column tube and the column tube away from the lower end/base assembly as these assemblies can weigh in excess of three tons. The use of heavy overhead lifting equipment to disassemble the column in order to carry out internal maintenance or inspection is not desirable. Operator safety is obviously a concern when heavy equipment is lifted overhead and technicians exposed below. Furthermore, alignment structures are required to keep the column and its base/adapter assemblies axially aligned as they are separated from each other, to avoid damage to the precision components.

The presence of such alignment and lifting structures creates significant obstructions around the tube and the need to be carefully laid out to provide sufficient clearance at some point of the circumference for insertion/removal of the internal components. Furthermore, the requirement to use heavy lifting equipment imposes constraints on housing such columns, sufficient overhead space and support being required to accommodate hoists or cranes. As many chromatography columns are now run in "clean" environments under GMP, to avoid microbiological contamination, where it is extremely difficult to accommodate overhead equipment, the requirement of moving the column to another room for disassembly and maintenance is problematic. This problem is exacerbated by the need to clean and verify the column before returning it for use to the clean environment. The presence of hoists or cranes in GMP facilities used for biopharmaceutical manufacturing is thus highly undesirable for the above mentioned reasons, together with the fact that these machines shed particulate matter, in the form of dirt, during their operation and maintenance.

U.S. Pat. No. 6,736,974 addresses some of the above problems by providing a column which is capable of lifting the adapter assembly above the column tube and/or raising the column tube above the base assembly by means of an hydraulic system which is integral to the column.

However, the system described in U.S. Pat. No. 6,736,974 has significant disadvantages associated with it by virtue of its design. As can be seen from FIGS. 4 and 5 of U.S. Pat. No. 6,736,974 and described in column 4, lines 63-66 of that document, in order to remove the distributor plate (31) and/or mesh (28/60) from the interior of the column, the operator must work within the centre of the drum (18) to access and remove the fixing nut (30) which secures these component parts. As industrial columns can have diameters ranging from about 200 mm to 2000 mm, typically within the range of 600 mm to 1400 mm, this means that the operator must work below a suspended or supported load to unscrew the nut. This clearly poses a significant safety risk to the operator, particularly where the operator's arm or head is exposed below the suspended or supported load.

Furthermore, once the column tube/cylinder or adapter assembly has been raised from the base assembly or tube, respectively, removal of the heavy bed support and/or distributor from the column can only be accomplished by tilting the bed support or distributor at an angle to negotiate the hydraulic drive pistons or safety rods. This can clearly be seen from, for example, FIGS. 3, 4 and 5 of U.S. Pat. No. 6,736,974 in which the distance between any two safety rods (69) or between any two hydraulic pistons (36) is less than the diameter of the mesh (28/60) or distributor plate (31). The same problem would exist for the base or adapter bed support (not shown). Removal of these internal components, which could weigh in excess of 100 kg, requires considerable manhandling by the operator and necessitates their being exposed below the suspended column or adapter assembly. Once again, this represents a significant safety risk for the operator.

The task of physically removing the heavy bed support or distributor, as described in U.S. Pat. No. 6,736,974, must be carried out by an operator, there being no disclosure of the use of any lifting aid to assist in this task. The configuration of the hydraulic pistons and the safety rods, and the need to tilt the bed support and/or distributor in order to avoid hitting these supporting structures in withdrawing these components from the column, would require the design of a bespoke lifting device.

Furthermore, the method described in U.S. Pat. No. 6,736,974, necessitates raising the column tube/cylinder or adapter assembly from the base assembly or tube, respectively, a predetermined distance greater than three inches in order to carry out maintenance of the column, distances greater than six inches and most preferably about twelve inches being specified.

WO 2005/056156 (Euroflow (UK) Limited) also discloses a column which can be accessed for maintenance without the need for a crane or hoist. The column is designed such that the tube and the base assembly can be separated by means of hydraulic drive cylinders to provide an access space between them to conduct maintenance or service on the base assembly. The piston of the adapter assembly can be advanced through the column tube to expose it at the open end of the column tube, i.e. in the space between the tube and the base assembly, for maintenance.

However, as is evident from this document (for example, FIGS. 19 and 20 and related description on page 23) access to release the fastening screws retaining the bed support or mesh in place is provided by the space between the tube and the base assembly. Removal of the bed support necessitates the operator being exposed to a suspended load while retaining screws are removed. Furthermore, the distance between any two drive cylinders for maintenance access is less than the diameter of the bed support (see, for example, FIG. 7), which requires the operator to manhandle and tilt the bed support when removing or replacing it. Maintenance of the column thus imposes a significant safety risk for the operator.

Applicant's co-pending patent applications U.S. Ser. No. 11/763,477 (U.S. publication number 2008-0308498) and PCT/SE2009/000011 (international publication number WO 2009/093952), the contents of which are incorporated by reference, describes chromatography columns and maintenance methods which do not require a crane or hoist for disassembly. The maintenance methods described in those patent applications provide improved operator safety by reducing the need for the operator to work below a suspended or supported load within the column. However, the removal and insertion of bed supports by the methods described in these documents requires considerable skill and/or strength by the operator to avoid damage by contact with other column components during the removal or installation process. These processes, which may involve the use of a lifting device, may be hampered by uneven or sloping floors in the production suite. Furthermore, the tube and the base, or the adapter assembly and the tube, must be raised a sufficient distance apart to allow access by an arm of a lifting device for removal or installation; this affects both the stroke length and cost of the cylinders. There thus remains a need to provide alternative cost-effective maintenance and/or inspection methods which are safer and easier for operators to use and which do not expose them to a suspended or supported load, thereby reducing the risk of operator error and injury.

SUMMARY OF THE INVENTION

The present invention recognizes and addresses these needs and others.

In a first aspect of the present invention, there is provided a method for conducting maintenance on a chromatography column or parts thereof comprising the steps of:
a) providing a chromatography column comprising:

a dispersion system comprising a nozzle including a mobile phase pathway connected to a liquid inlet;
a tube with an adapter assembly connected to an integrated drive system, said adapter assembly moveable within a cavity of said tube in an operational mode;
the adapter assembly comprising a backing plate, a distributor and a bed support fastened to each other by releasable fixing means,
a collection system opposing the dispersion system; and one or more seals;
b) disconnecting the adapter assembly from the tube;
c) lifting the adapter assembly above the tube with the drive system to provide a gap for access therebetween;
d) affixing guide elements to the tube;
e) unfastening the bed support from the distributor and said backing plate without accessing the interior of the column;
f) removing the bed support from the column without accessing the interior of the column by means of said guide elements;
g) conducting maintenance on the column and/or the bed support and/or said one or more seals;
h) returning the bed support to the column and fastening the bed support and the backing plate to the distributor without accessing the interior of the column;
i) releasing the guide elements from the tube; and
j) lowering the adapter assembly to an operational position within the tube and reconnecting the adapter assembly to the tube.

It will be understood by the skilled person that step d), affixing the guide elements to the tube could be carried out after step e); similarly step j) could be carried out before step i).

In one aspect, step c) involves lifting the adapter assembly a distance of no more than three inches or seventy six millimeters above the tube with the drive system to provide a gap for access there between. The gap provided for access between the adapter assembly and the tube is no more than three inches or seventy-six millimeters in height in order to permit removal of the bed support from the column or return thereto.

Optionally, step c) involves lifting the adapter assembly a distance of no more than two inches or fifty millimeters above the tube with the drive system to provide a gap for access to the column. In another aspect, the gap is less than two inches or fifty millimeters in height. In a further aspect, the gap is one inch or twenty-five millimeters in height. Restriction of the gap height to less than three inches or seventy-six millimeters prevents the operator from working beneath the raised adapter assembly and being physically exposed to the suspended weight.

In another aspect, the guide elements are guide rails. In other embodiments, the guide elements may take the form of bumpers or vertically mounted rollers or other technical means which restrict the bed support from traveling in any direction other than the direction intended for removal or insertion.

In a further aspect, step f) and/or step h) additionally comprises using transfer means to move the bed support along the guide elements.

In a further aspect, the transfer means is a roller plate. Other embodiments, such as an assembly of rollers or balls which facilitate the sliding of the bed support along the guide element and thus out from or into the column are possible.

In one aspect, step d) additionally comprises affixing the guide elements to a support. The support can, for example, be any body or structure which allows the guide elements both to sustain the weight of the bed support or distributor and to maintain a horizontal or level position to facilitate removal of the bed support or distributor from the column. In one embodiment, the support is a handling device. The handling device may comprise at least one arm and the method comprises supporting the bed support on or releasably affixing the bed support to at least one arm of the handling device.

It should be noted that the fixing means are releasable from the exterior face of the distributor. This reduces the exposure of the operator to a suspended or supported load as they do not need to enter the gap.

The integrated drive system is an electric, motorized, hydraulic or pneumatic system. In a preferred aspect, the drive system comprises at least two cylinders and the distance between any two cylinders for maintenance access is greater than the diameter of the bed support. This permits the use of a handling device to support and remove or replace the bed support and/or distributor from/to the column. This arrangement also allows removal or insertion of the bed support without the need for substantially tilting it. This reduces operator exposure beneath the suspended load and facilitates manhandling and/or mechanical handling of the bed support. More preferably, each cylinder is independently removable from the column.

According to a second aspect of the present invention, there is provided a method for conducting maintenance on a chromatography column or parts thereof comprising the steps of:
a) providing a chromatography column comprising:
   a dispersion system comprising a nozzle including a mobile phase pathway connected to a liquid inlet;
   a tube with an adapter assembly and a base assembly connected to an integrated drive system, said adapter assembly moveable within a cavity of said tube in an operational mode;
   said base assembly comprising a distributor, a backing plate and a bed support fastened to each other by releasable fixing means;
   a collection system opposing the dispersion system; and one or more seals;
b) releasing the tube from the base assembly;
c) lifting the tube and the adapter assembly above the base assembly with the drive system to provide a gap for access there between;
d) affixing guide elements to the tube;
e) unfastening the bed support from the distributor and said backing plate without accessing the interior of the column;
f) removing the bed support from the column without accessing the interior of the column by means of said guide elements;
g) conducting maintenance on the column and/or the bed support and/or said one or more seals;
h) returning the bed support to the column and fastening the bed support to the backing plate and to the distributor without accessing the interior of the column;
i) releasing the guide elements from the tube; and
j) lowering the tube and the adapter assembly to an operational position and reconnecting the tube to the base assembly.

It will be understood by the skilled person that step d), affixing the guide elements to the tube could be carried out after step e); similarly step j) could be carried out before step i).

In one aspect, step c) involves lifting the tube and the adapter assembly no more than three inches or seventy six millimeters above the base assembly with the drive system to provide a gap for access there between.

In another aspect, step c) involves lifting the tube and the adapter assembly no more than two inches or fifty millimeters above the base assembly with the drive system to provide a gap for access there between. In a further aspect, the gap is one inch or twenty-five millimeters in height. Restriction of the gap height to less than three inches or seventy-six millimeters prevents the operator from working beneath the raised adapter assembly and being physically exposed to the suspended weight.

In another aspect, the guide elements are guide rails. In other embodiments, the guide elements may take the form of bumpers or vertically mounted rollers or other technical means which restrict the bed support from traveling in any direction other than the direction intended for removal or insertion.

In a further aspect, step f) and/or step h) additionally comprises using transfer means to move the bed support along the guide elements. The transfer means may, for example, be a roller plate. Other embodiments, such as an assembly of rollers or balls which facilitate the sliding of the bed support along the guide element and thus out from or into the column are possible.

In another aspect, after step e) the bed support is raised above the distributor by lifting means attached to the backing plate. In one embodiment the lifting means comprises a movable cam plate with a beveled edge for reversible insertion between the bed support and the distributor. In another embodiment, the lifting means comprises a rotatable semi-circular cam plate.

In one aspect, step d) additionally comprises affixing the guide elements to a support. The support can, for example, be any body or structure which allows the guide elements both to sustain the weight of the bed support or distributor and to maintain a horizontal or level position to facilitate removal of the bed support or distributor from the column. In one embodiment, the support is a handling device. The handling device may comprise at least one arm and the method comprises supporting the bed support on or releasably affixing the bed support to at least one arm of the handling device.

The integrated drive system is an electric, motorized, hydraulic or pneumatic system. In a preferred aspect, the drive system comprises at least two cylinders and the distance between any two cylinders for maintenance access is greater than the diameter of the bed support. This permits the use of a handling device to support and remove or replace the bed support and/or distributor from/to the column. This arrangement also allows removal or insertion of the bed support without the need for substantially tilting it. This reduces operator exposure beneath the suspended load and facilitates manhandling and/or mechanical handling of the bed support. More preferably, each cylinder is independently removable from the column.

In one embodiment, the column comprises a locking system which mechanically secures the cylinders of the drive system in place and immobilizes them so movement of the adapter becomes impossible in case of a failure of the drive system. The method further comprises the step of locking the adapter assembly and the tube above the base assembly with the locking system after lifting the adapter assembly and the tube no more than three inches or seventy-six millimeters above the base assembly with the drive system. This provides for greater operator safety.

According to a third aspect of the present invention, there is provided a chromatography column suitable for carrying out the method of the first and/or second aspect of the invention.

BRIEF DESCRIPTION OF THE DRAWINGS

The features and advantages of the invention will become apparent from the following description taken in connection with the accompanying drawings in which:

FIG. 4b is a side sectional view of the column of FIG. 4a.

FIG. 4c is a top plan view of the column of FIG. 4a.

DETAILED DESCRIPTION OF THE PREFERRED EMBODIMENTS

Figure 1:
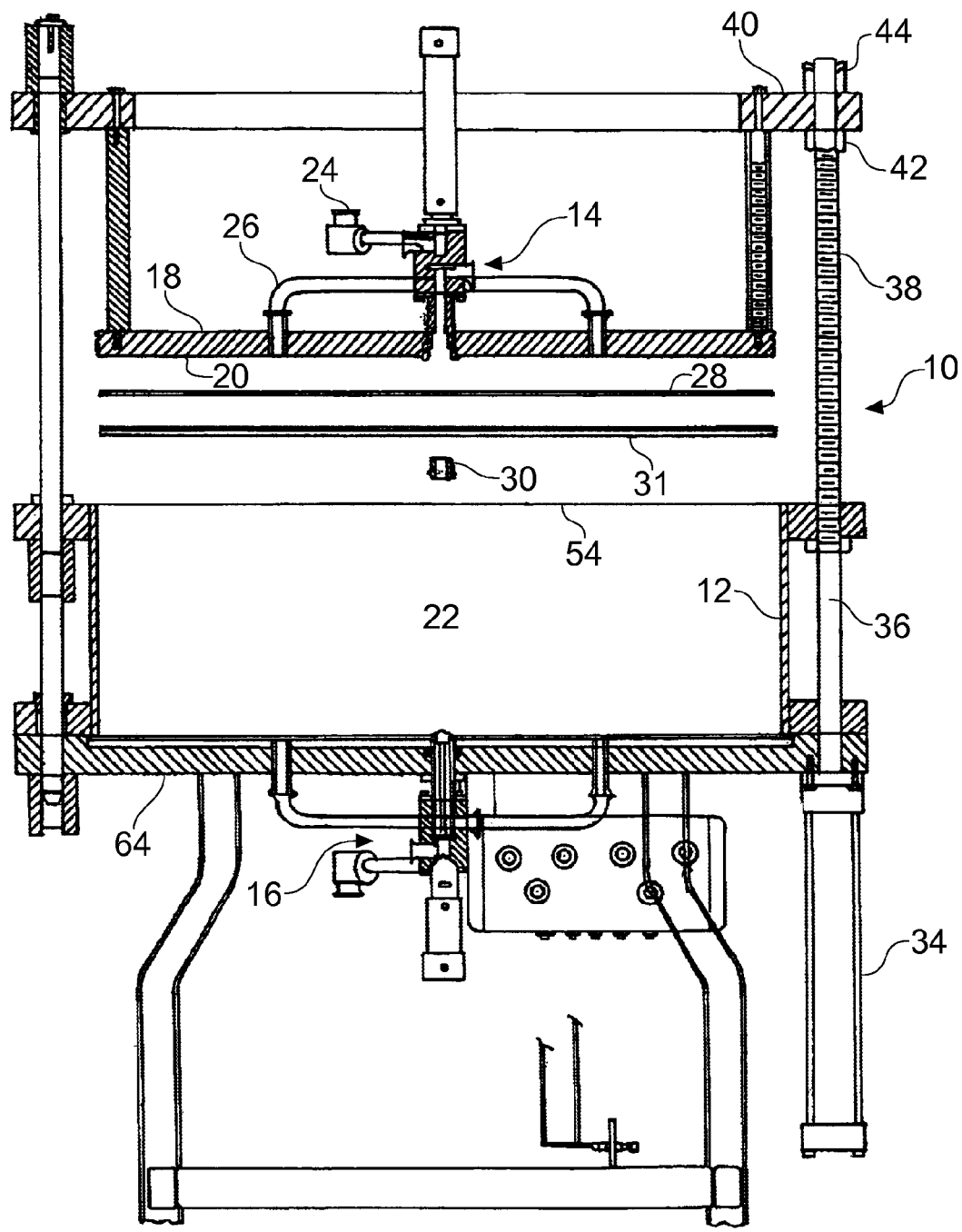
FIG. 1 shows an embodiment of a column known in the art in a first maintenance position in cross sectional view.

The present invention is concerned with a method and apparatus for enabling maintenance within a chromatography column. FIG. 1 shows a column 10 known in the art and described in U.S. Pat. No. 6,736,974 which permits maintenance within a chromatography column without the need for a hoist or crane. The column 10 comprises an elongated hollow cylindrical housing 12, or tube, having a dispersion system 14 at the top and a collection system 16 at the bottom. The dispersion system 14 includes a cylindrical drum 18 having an upper cylindrical plunger head or adapter 20 formed at the lower or interior end (i.e. interior to the column). The adapter 20 is normally disposed within the upper portion of tube 12 such as is illustrated in the first operational position of FIG. 1. The adapter 20 may be moved by a drive system 34 such as the hydraulic arrangement shown in FIG. 1. The movement of the adapter 20 allows for the compression of chromatography media in order to produce a packed media bed of the optimum height within the column; a cavity 22 is formed between the dispersion and collection systems 14, 16 and/or between the adapter 20 and the base 64.

The dispersion system 14 may include a mobile phase pathway connected to a liquid inlet 24 together with an inlet manifold 26 to distribute incoming liquid throughout a top portion of a media bed contained within the cavity 22. A bed support (or inlet screen) 28 or filter is attached to the adapter 20 by connectors and/or by an inner clamp nut 30 which is accessible from the cavity 22. The bed support 28 may be removed for maintenance purposes by release of the clamp nut 30; the distributor plate 31 may also be removable (see U.S. Pat. No. 6,190,560 for a description of a distributor plate design).

A drive system is used to move the adapter 20 in an operational mode. The drive system is comprised of at least one and preferably three or more, drive cylinders 34. The drive cylinders 34 move drive pistons 36 which are coupled to the drum 18. A portion of the drive pistons 36 may by threaded 38 to allow for the drive piston 36 to connect or couple to connection arms 40 at specific locations relative to the drive piston 36 such as with nuts 42, 44.

FIG. 1 shows a first maintenance position of the adapter 20 wherein the adapter 20 is raised a predetermined distance from a top 54 of the cavity 22 within the cylinder by means of the drive system 34 and piston 36. The operator is thereby provided access with a hand to the centre of the drum 18 to release or affix nut 30 which retains the distributor plate 31 and bed support 28 to the adapter 20. The distributor plate 31 and or/bed support 28 may then be removed for maintenance. These are then replaced by affixing them to the adapter 20 and the adapter 20 may be lowered to return to an operational mode, nuts 42, 44 being reset to a proper operational configuration, if necessary.

Figure 2:
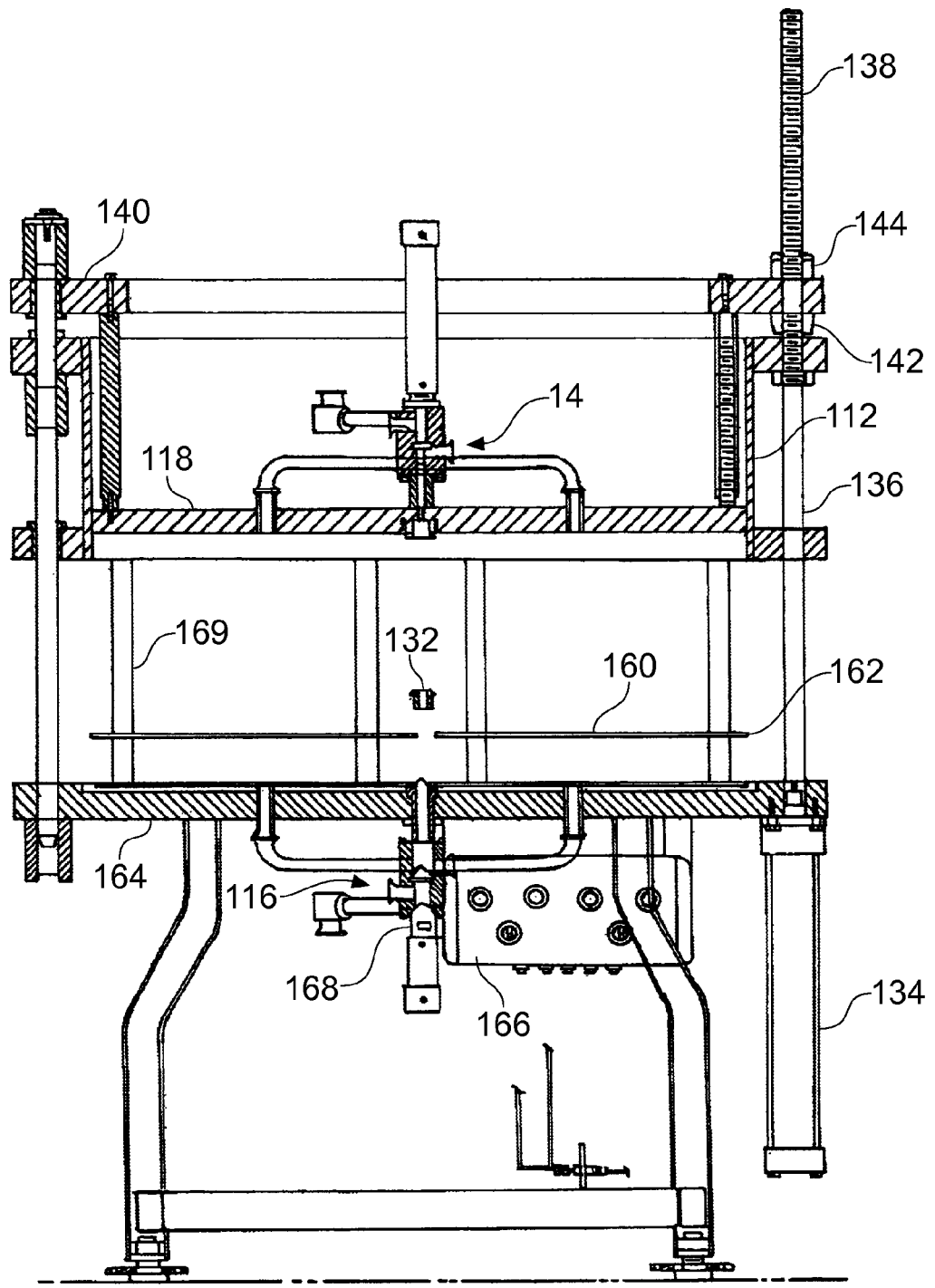
FIG. 2 is a cross sectional view showing the same embodiment of the column of FIG. 1 in a second maintenance position.

In order to perform a second maintenance operation, such as removal of the lower bed support (or screen) 160 which is typically positioned so that its outer edge 162 is between the tube 112 and the collection system 116, the tube 112 may be raised by the drive system as illustrated in FIG. 2. The bolts which normally secure the tube 112 to the base 164 are removed, and the nuts 142, 144 may be coupled to the piston 136 to drive the tube 112 along with the drum 118 upwards as shown. A gap is thus provided which allows access for an operator to loosen nut 132, which affixes the bed support 160 to the base 164, and remove the bed support 160 for maintenance. Once maintenance has been completed, the bed support 160 is replaced, affixed by nut 132 to the base 164 by the operator, and the process reversed to lower tube 112 and the drum 118 into an operational position.

The present invention will now be described with reference to FIGS. 3 to 13; FIGS. 3 to 8 relate to providing access to the upper adapter assembly and FIGS. 9 to 13 to providing access to the base assembly for maintenance.

Figure 3:
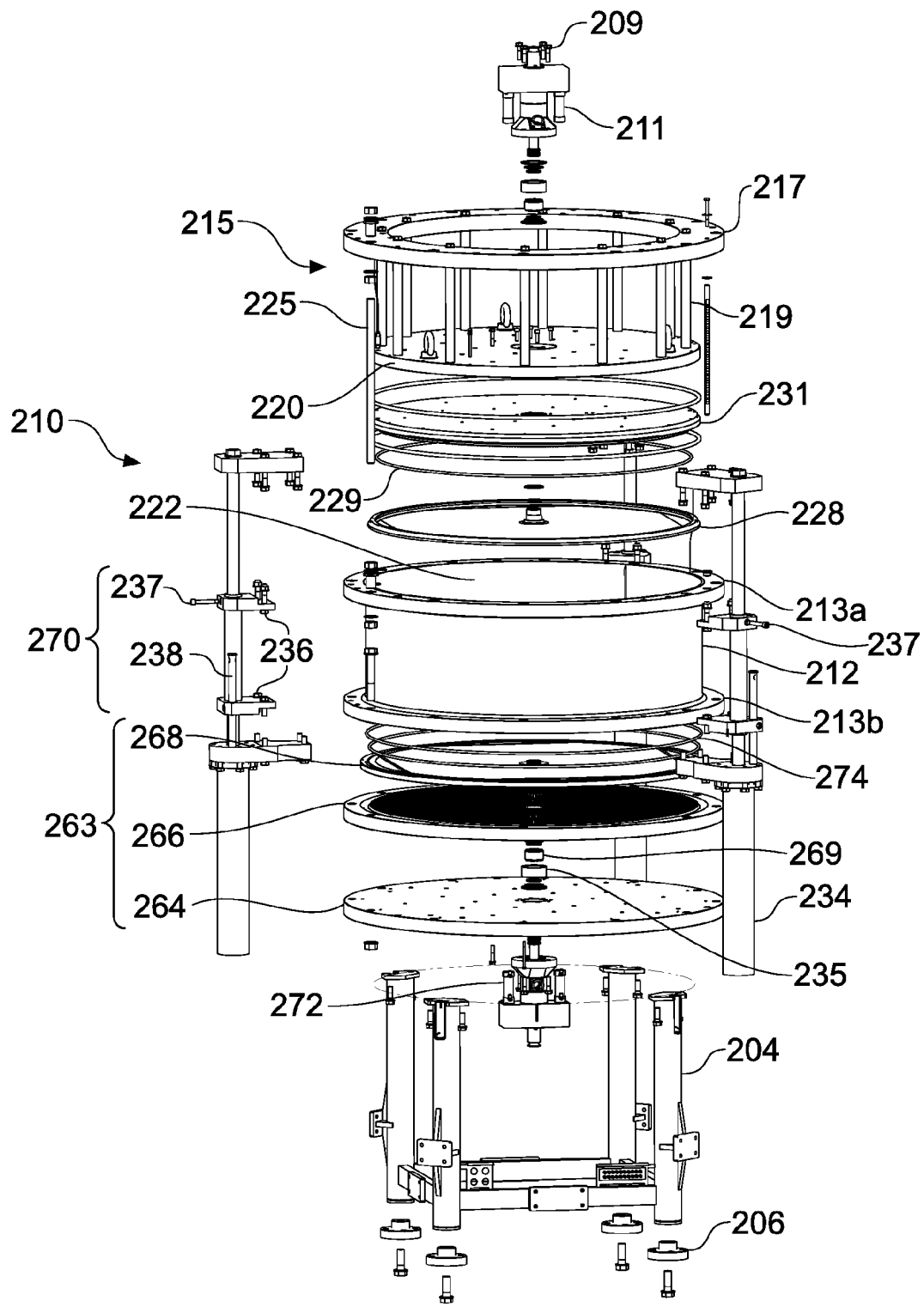
FIG. 3 is a schematic exploded front view of an embodiment of the present invention.

FIG. 3 is a schematic exploded front view of a column in accordance with the invention. The column is made of strong, inert materials such as stainless steel and other materials which are suitable for use in a GMP environment typical of the pharmaceutical industry. The column 210 is supported on legs 204 having feet 206 which are adjustable in order to modify the height and/or the level of the column. The legs 204 support the column 210 which comprises a cylindrical housing or tube 212 separating a base assembly 263 at one end from an adapter assembly 215 at the other. The tube 212 may typically be made from stainless steel, or other strong, inert materials. Adjacent to the adapter assembly 215 is a dispersion system comprising a nozzle 211 which includes a mobile phase pathway, for the introduction of buffer or other suitable mobile phase liquids or chemicals/materials to be separated, and a liquid inlet 209. The tube 212 may be connected to the adapter assembly 215 and base assembly 263 by a drive system having one or more cylinders 234. The drive system may be a hydraulic system, as shown, or may be powered by other suitable means, such as pneumatic or electrical means. The adapter assembly 215 is moveable within a cavity 222 of the tube 212 in an operational mode, for example, to pack or compress the bed of chromatographic media used to effect chromatographic separation of chemicals within the column. The adapter assembly 215 comprises an adapter flange 217, one or more distance pillars 219, a backing plate 220 made typically of stainless steel, a distributor 231 which may take the form of a plate having many channels to effect the even distribution of liquids, and a bed support 228 comprising a screen or mesh or filter and optionally a sealing ring (e.g. 229). The bed support may be made of an inert plastic or metal material such as stainless steel. The distributor 231 and bed support 228 are fastened to each other by releasable fixing means (not shown). Typical releasable fixing means include, but are not limited to, a screw, a nut or a clamp. The fixing means (not shown) may only be accessed and thus released from the exterior face of the distributor 231 or backing plate 220, that is the face of the plate furthest away from the cavity 222. In the present example, the nozzle 211 must first be removed to provide access to the fixing means (not shown). Additional releasable fixing means, accessible from the exterior face of the backing plate, may optionally be employed to fasten the backing plate, distributor and bed support together. These fixing means can take the form of bolts inserted through corresponding holes around the perimeter of the components. Access from the exterior face of the backing plate or distributor avoids unnecessary exposure of the operator to a suspended or supported load within the column.

The base assembly 263 comprises a distributor 266 and a bed support 268 and optionally a backing plate 264 fastened to each other by releasable fixing means 269. The bed support 268 comprises a screen or mesh or filter and optionally a sealing ring (e.g. 274). The bed support may be made of an inert plastic or metal material such as stainless steel. Releasable fixing means 269 are, for example, a screw, a nut, a bolt or a clamp; it will be appreciated that other releasable fixing means are also possible. As can be seen from the figure, the fixing means 269 secures bed support 268 and the distributor 266 through a central hole in each component. The fixing means 269 is only accessible and may therefore only be released from the exterior face of the distributor 266. In FIG. 3, nozzle 272 must first be removed to provide access to release fixing means 269. Additional releasable fixing means, accessible from the exterior face of the backing plate, may optionally be employed to fasten the backing plate, distributor and bed support together. These fixing means can take the form of bolts inserted through corresponding holes around the perimeter of the components. Access from the exterior face of the backing plate 264 avoids operator exposure beneath a suspended load, were access only to be available from within the interior of the column.

It will be understood that separation of chemical or biological materials on the column, when the tube 212 is full of chromatographic media, can be carried out in either a downward or upward flow. Thus, in a downward flow, liquid containing chemical or biological materials to be separated is introduced through nozzle 211 and moves in a downward direction through the bed of media, to be collected in the collection system at the base of the column through nozzle 272 via an outlet port (375 in FIG. 4b). In upward flow mode, liquid containing materials to be separated is introduced via the bottom nozzle 272 and flows upwards through the media bed to be collected at the top of the column through nozzle 211 via an outlet port (305 in FIG. 4b). In the interests of clarity, the maintenance or servicing of the column will be described in downward flow mode.

In order to conduct maintenance on the adapter assembly 215 or distributor 231, the adapter assembly 215 is disconnected from the column tube 212 by unscrewing the nuts which join the adapter flange 217 to the upper column flange 213a. The drive system then raises the adapter assembly 215 a distance of no more than three inches or seventy six millimeters, typically a distance of no more than two inches or fifty millimeters by means of cylinders 234 to allow provide a gap through which the bed support 268 and/or distributor 266 can be removed. The adapter assembly 215 is locked into position using the locking system 270 by means of plungers 237 which are inserted through aligned holes in the cylinder bracket 236, cylinder 234 and assembly 215. In this secured position, the adapter bed support and/or the distributor may be removed from the column for maintenance once the fixing means are released, release being effected by removal from the exterior face of the column following removal of the nozzle 211 as described above. Once maintenance has been carried out on the column (e.g. the bed support 228 has been replaced), the column 210 is made operational again by reversing the above procedure: the adapter assembly 215 is released from its secured position by removal of the plungers 237 and lowered by use of cylinders 234 to be reconnected to the column tube 212 by replacing the nuts which join the adapter flange 217 to the upper column flange 213a.

Maintenance or service is carried out on the bottom distributor 266 or base assembly 263 by releasing the tube 212 from the base assembly 263 and lifting the tube 212 and adapter assembly 215 a distance of no more than three inches or seventy-six millimeters, typically a distance of no more than two inches or fifty millimeters, with the aid of the drive system. The bolts on the lower flange 213b of the column tube 212 which join it to the bottom backing plate 264 are removed. The column tube 212 and adapter assembly 215 are then lifted by means of the drive cylinders 234. The tube 212 and upper adapter assembly is secured in position by the locking system 270 above the base with the cylinder brackets 236 by inserting a plunger (not shown) through holes aligned in the locking pin 238 and bracket 236.

The bottom nozzle 272 is then disconnected from the back plate 264 and distributor 266. The nozzle 272 is removed together with the distance ring 235, to allow access to release the fixing means 269 which may be in the form of a nut. The nut 269 is removed from the exterior face of the distributor 266, i.e. the face distant from the cavity 222, and thus eliminates operator exposure to a suspended or supported load. If additional releasable fixing means, such as bolts inserted through the backing plate, distributor and bed support as described above are present, these must be removed from the exterior face of the backing plate. The interior of the column may now be accessed for maintenance or service, such as the replacement or cleaning of the bed support 268 and/or O-rings. To return the column to an operational mode, the above procedure is reversed.

Figure 4B:
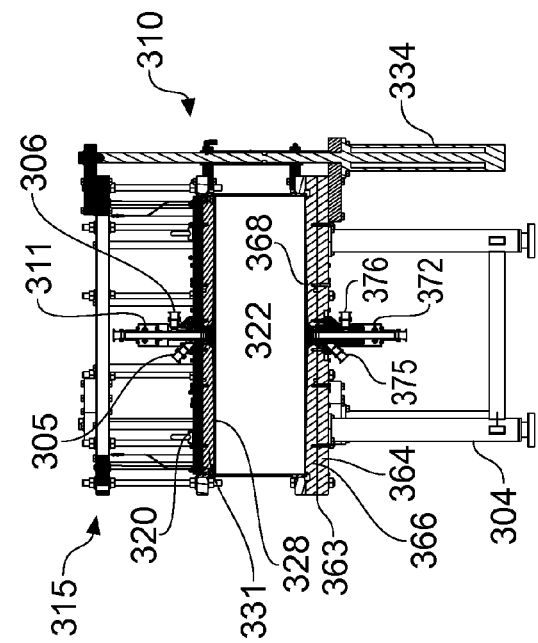
Figure 4A:
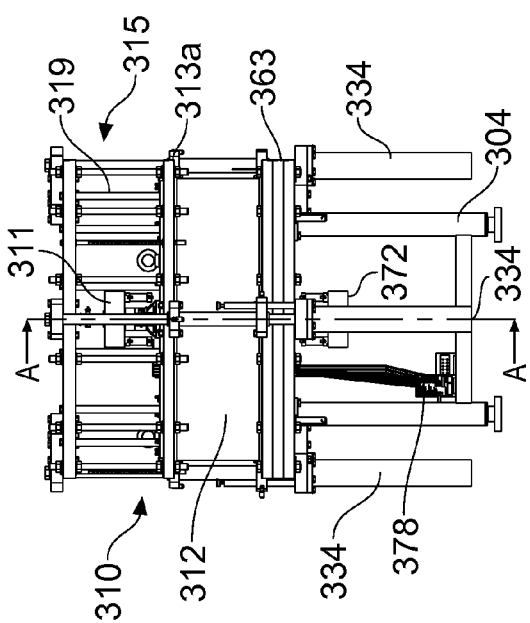
FIG. 4a is a schematic front view of a column in accordance with the invention.

FIG. 4a is a schematic front view of a column in accordance with the invention. The column 310 is supported on legs 304 and has a base assembly 363 separated from an adapter assembly 315 by a tube 312. These components are made of strong, inert materials which are approved for GMP within the pharmaceutical industries, such as stainless steel. In the figure, the base assembly 363 and adapter assembly are connected to a drive system which takes the form of three hydraulic cylinders 334. It will be understood that in other embodiments, different drive systems may be used to raise and lower the column, such as those powered by compressed air or electricity. Furthermore, it is not essential that three cylinders are used, in some cases one being sufficient. The column 310 has a top nozzle 311 and a bottom nozzle for the introduction of liquids into the column. An hydraulic assembly 378 attached to drive system/cylinders 334 is also shown.

FIG. 4b is a side sectional view of the column of FIG. 4a showing one of the hydraulic cylinders 334 in cross section. The cavity 322 for containing the bed of chromatographic media can be seen in cross section. The liquid inlet 305, 375 and outlet 306, 376 of the top 311 and bottom 372 nozzle are shown, for the introduction and removal of liquids from the column 310. The cylinder 334 is connected to the base assembly (seen here comprising backing plate 364, distributor 366 and bed support 368) and the adapter assembly 315 (seen here comprising backing plate 320, distributor 331 and bed support 328).

Figure 4C:
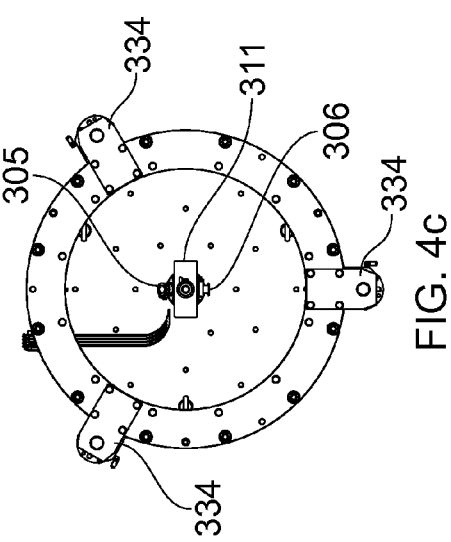

FIG. 4c is a top plan view of the column of FIG. 4a which shows the three hydraulic cylinders 334 and nozzle 311 with liquid inlet 305 and outlet 306.

To raise the adapter assembly 315 for maintenance purposes, the nuts under the upper column flange, which join the adapter 315 and column flange 313a, are loosened and removed. The drive system then lifts the adapter assembly 315 a distance of no more than three inches or seventy-six millimeters, typically a distance of no more than two inches or fifty millimeters, by means of the hydraulic cylinders 334. The adapter assembly 315 is raised until holes in the cylinder bracket (not shown), hydraulic cylinders 334 and the adapter assembly 315 are aligned and locked into position with plungers (not shown) to secure the assembly in the service or maintenance position (see FIG. 3).

Figure 5A:
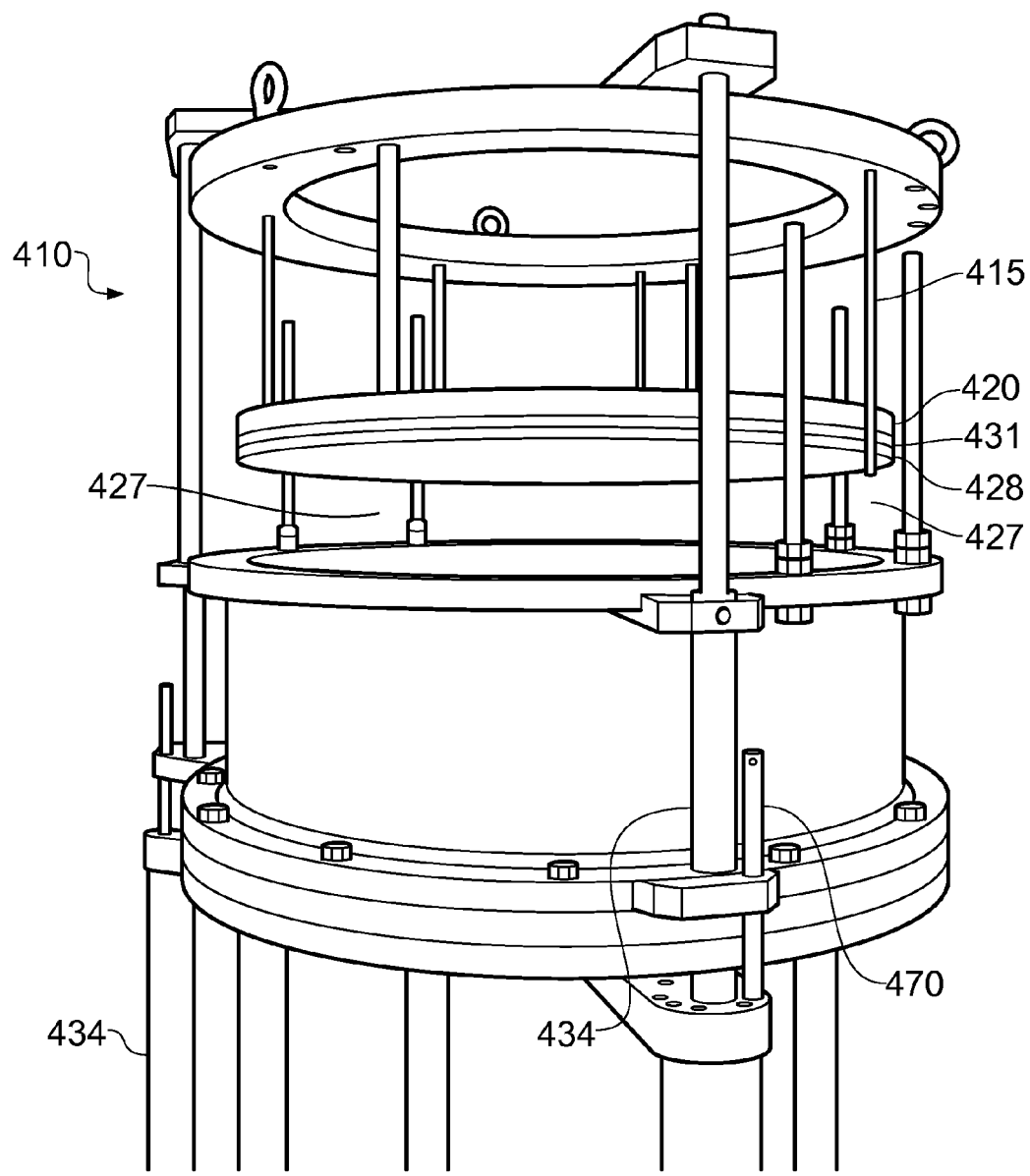
FIG. 5a is a front perspective view showing the adapter assembly raised and secured into position to provide a gap for access.

FIG. 5a is a front perspective view showing the adapter assembly 415 raised and secured into position to provide a gap 427 through which the bed support 428 and/or distributor 431 can be removed. The gap 427 is clearly shown in the figure for illustrative purposes but it would be no more than three inches or seventy-six millimeters and typically no more than two inches or fifty millimeters in size to prevent the operator inadvertently reaching into it and exposing his/her arm to a heavy suspended load. The column 410 has a drive system comprising three hydraulic cylinders 434. The adapter bed support 428, the distributor 431 and the backing plate 420 are now visible; the bed support 428 can be unfastened from the distributor 431 by releasing the fixing means (not shown) without accessing the gap 427. In order to describe this process, reference is made to FIG. 4 in that the nozzle 311 is first removed to provide access to remove the retaining nut (not shown) which secures the bed support 328 to the distributor 331 without accessing the gap 427. The fixing nut is removed from the exterior face of the distributor 331.

Figure 5B:
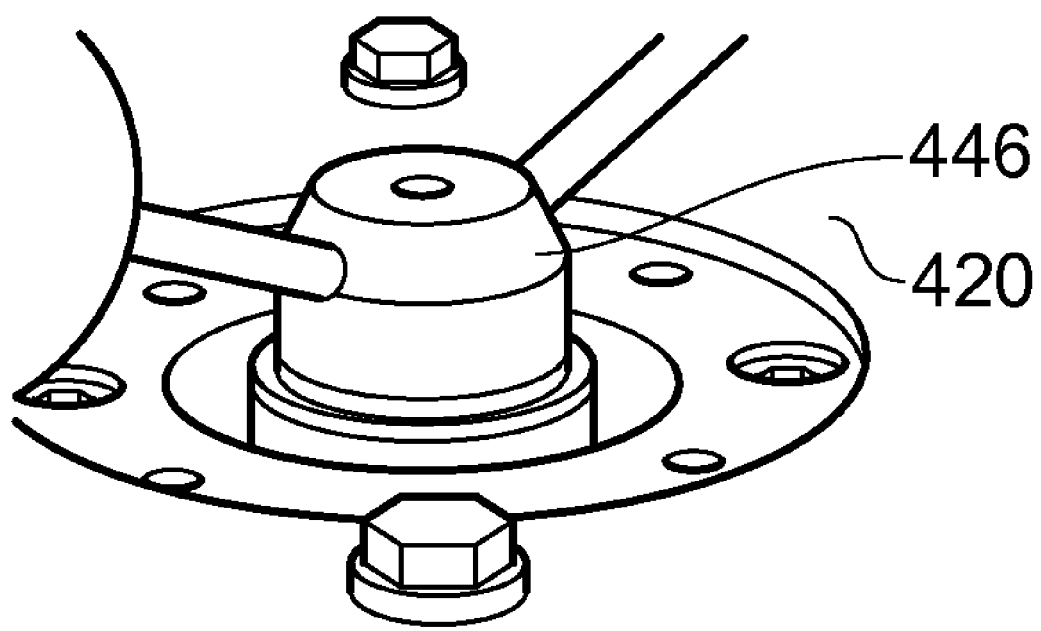
FIG. 5b shows removal of the fastening means securing the distributor and bed support.

FIG. 5b shows release of the fixing means from the backing plate 420 side of the adapter assembly using a spanner 446. The fixing means (in the form of a retaining nut, obscured by the spanner) secures the adapter bed support to the distributor.

Figure 6:
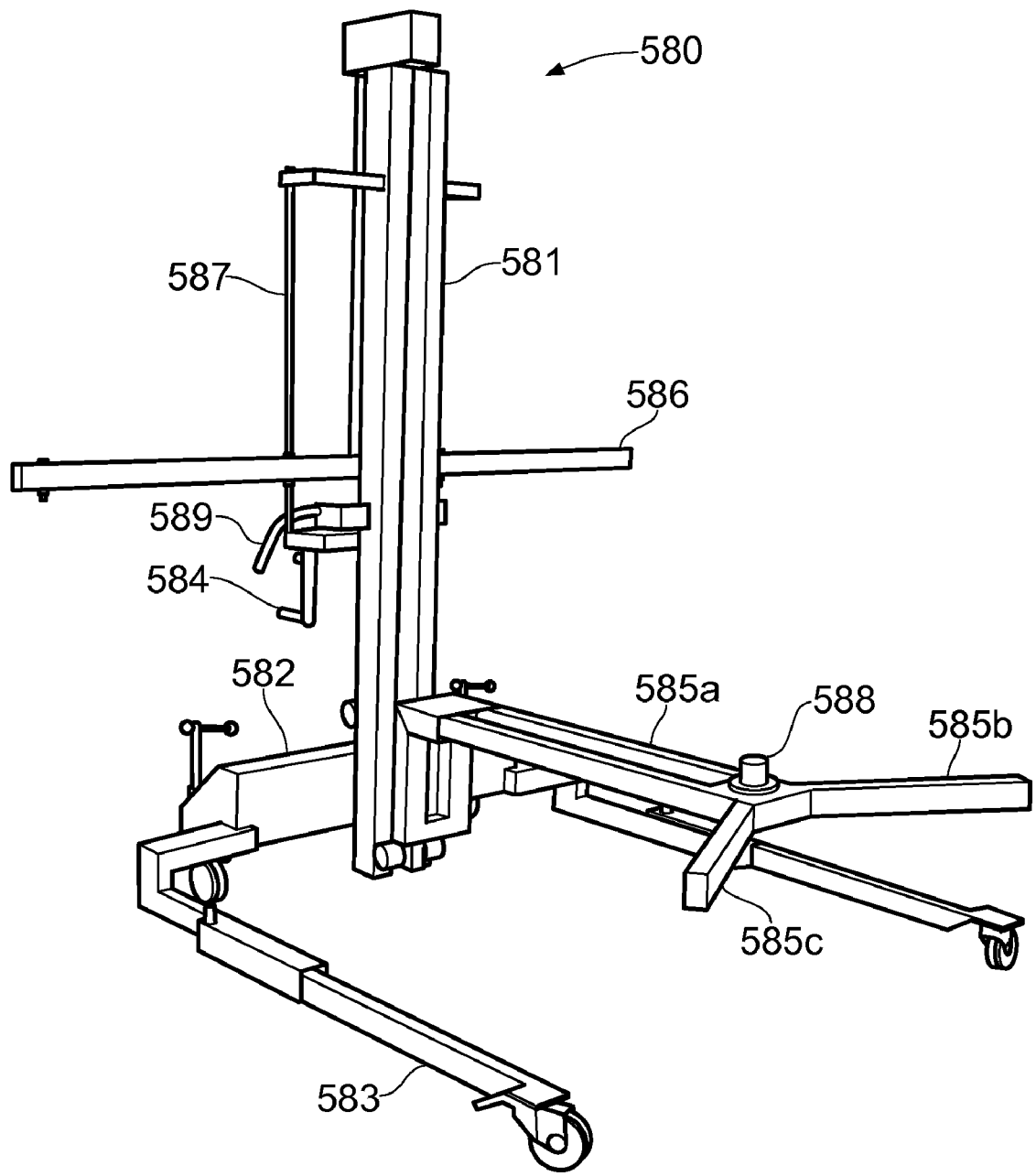
FIG. 6 is a perspective view of a handling device used to remove/insert a distributor or a bed support from/into a column in accordance with the invention.

An embodiment of a handling device 580 is shown in FIG. 6. The device 580 is in the form of a trolley or cart with a central pillar 581 supported on frame 582 having legs 583. The device 580 is made of strong, inert materials; such materials include, but are not limited to, stainless steel and other materials which are suitable for use in a GMP environment typical of the pharmaceutical industry. Extendable arms 585 a, b, c project from the pillar 581 and can be raised or lowered relative to the pillar 581 by mechanical or other means. In the embodiment shown, the arms 585 a, b, c are raised or lowered by a manual jacking mechanism 584 adjacent to the handle 589 which provides the means to steer or control the device. The arms 585 a, b, c are designed to bear the weight of the distributor or bed support and are extendable to the diameter of these components. While the embodiment shown has three arms 585 a, b, c, it will be understood that the device is not so limited and that other embodiments may have less than or more than three arms (e.g. one, two, four, five) depending on the individual design. Holes (not shown) at the extremities of the arms 585 a, b, c are provided for bolting or securing of the distributor and/or bed support to the arms for safety, particularly during transport. Pads (not shown) may be fitted to the arms 585 a, b, c to minimize any risk of damage to the bed support/distributor when these components come into contact with the arms. A raised, central element, 588 (typically of conical shape) for receipt of the central hole in the bed support or distributor provides a means for centralizing these components on the arms 585 a, b, c of the device 580. This element 588 may be fitted on either, or both, the upper or under side of the point where the arms 585 a, b, c intersect. Cross member 586 projects at right angles to pillar 581 and can be raised or lowered by use of lifting screws 587. The cross member 586 is used to support guide elements (not shown) which can be reversibly attached to the member 586 and to the column tube (not shown) to facilitate removal or insertion of the bed support.

In operation, the distributor and/or bed support is either suspended from the arms 585 a, b, c or supported on the arms. Pivotal wheels allow easy movement and maneuverability of the handling device 580. In the embodiment shown, the movement of the device 580 and the raising/extension of the arms 585 a, b, c are by manual means, but it will be understood that other embodiments are possible which incorporate powered systems (e.g. electrical, pneumatic or hydraulic systems) to drive the device 580 and lift/lower the arm 585

Other embodiments of the handling device are possible, for example in which the holes (not shown) at the ends of the arms 585 a, b, c are configured to align with corresponding holes in the side of the bed support or distributor when the arms 585 b, c contact the outer rim of these components, thereby allowing affixing of the bed support or distributor to the arms simply by means of threading screws into the aligned holes.

Figure 7A:
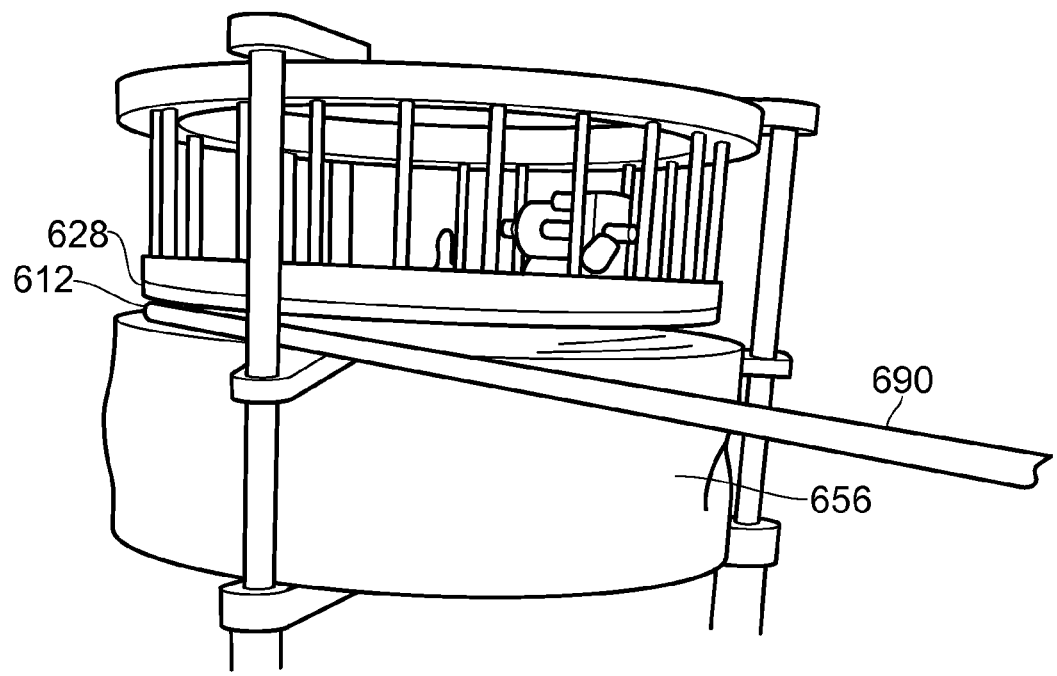
FIG. 7a is a perspective view of the column of FIG. 5 showing the attachment of guide elements or rails to the column tube.

FIG. 7a illustrates the guide elements 690 in the form of rails being attached to the column tube 612 upper flange, the column tube being covered by protective plastic 656. The rails 690 are positioned just below the bed support 628 such that the support can be gently lowered to a position above the rails 690 following the removal of any fixing means (e.g. screws).

Figure 7B:
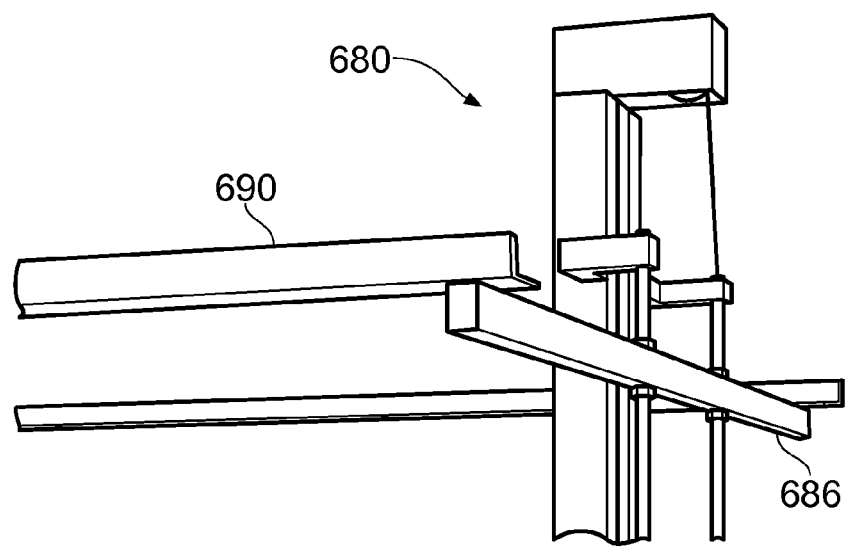
FIG. 7b illustrates the attachment of the other end of the guide elements or rails to the cross member of a handling device.

The height of the cross member 686 of the handling device 680 is adjusted to match that of the protruding guide elements or rails 690 and the rails 690 and cross member 686 are then secured to each other (FIG. 7b).

Figure 8A:
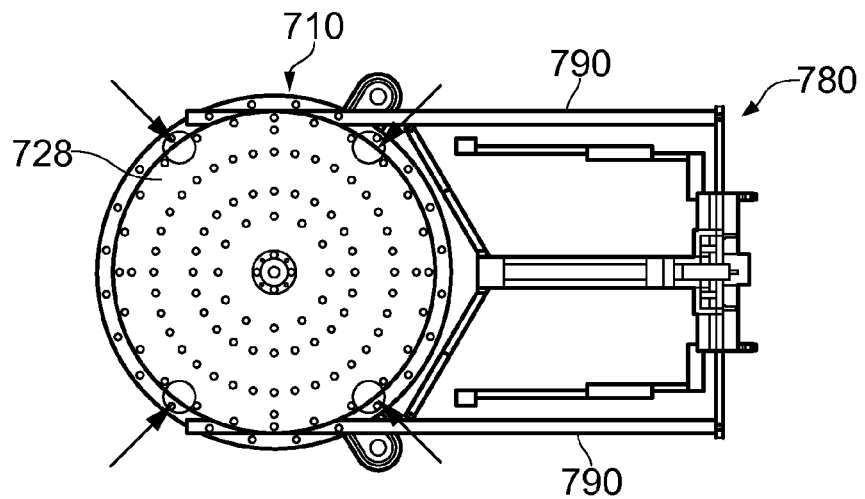
FIG. 8a is a sectional schematic plan view of the column of FIG. 5, following attachment of the rails to the column tube and the cross member, with the handling device in position to support the bed support.
Figure 8B:
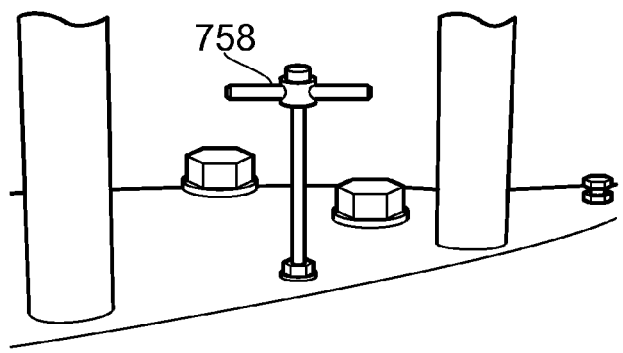
FIG. 8b is a perspective view of the column showing one of the lifting screws in position which are used to lower the bed support from the adapter.
Figure 8C:
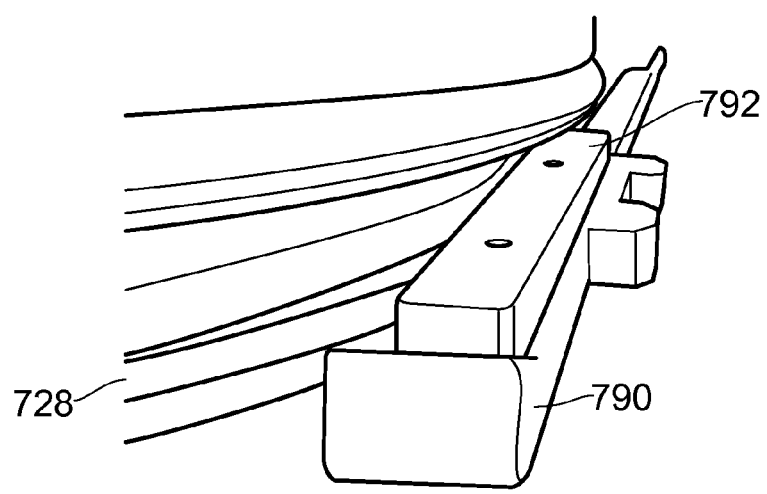
FIG. 8c is a perspective view of the column showing the roller plate attached to the adapter bed support and positioned within the rails.

FIG. 8a is a schematic plan view of a section of the column 710 showing the handling device 780 positioned to receive the bed support 728; the position of the first four screws to be removed that secure the bed support to the adapter is indicated by the arrows. These four screws are removed and replaced with four lifting screws (not shown) which are used to lower or raise the bed support on removal of the remaining retaining screws. Once all of the retaining screws have been removed, the bed support 728 is gently lowered orthogonally by means of lifting screws 758 (FIG. 8b) until it is approximately 10 mm above the surface of the rails 790. The O-ring is lifted from the outer rim of the bed support and pushed under the distributor to avoid contact with the transfer means which are to be inserted (not shown). The transfer means 792 (or roller plates in the embodiment shown) are affixed to the bed support 728 and the support 728 is gently lowered until the roller plates 792 are firmly resting on the rails 790 (FIG. 8c). It will be understood that other embodiments are possible in which the bed support 728 could simply be lowered onto the transfer means or roller plates 792 which are resting on the rails 790 without affixing the bed support to the roller plate.

Figure 9A:
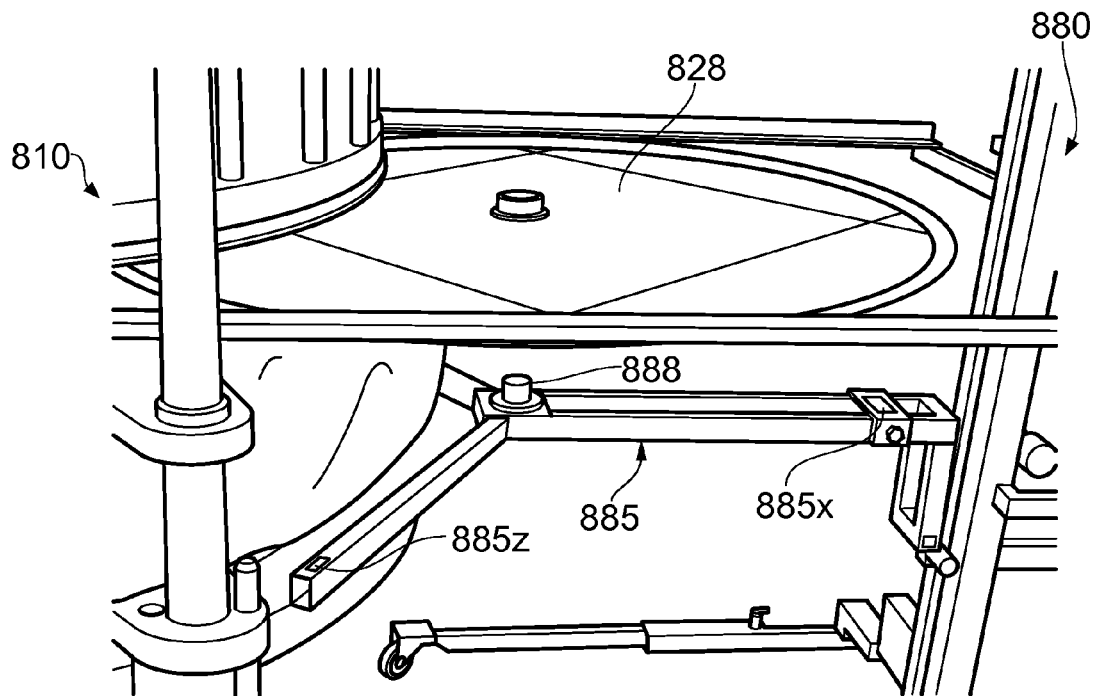
FIG. 9a is a perspective view of the column of FIG. 5 with the adapter bed support partially removed from the column and in alignment with the arms of the handling device.
Figure 9B:
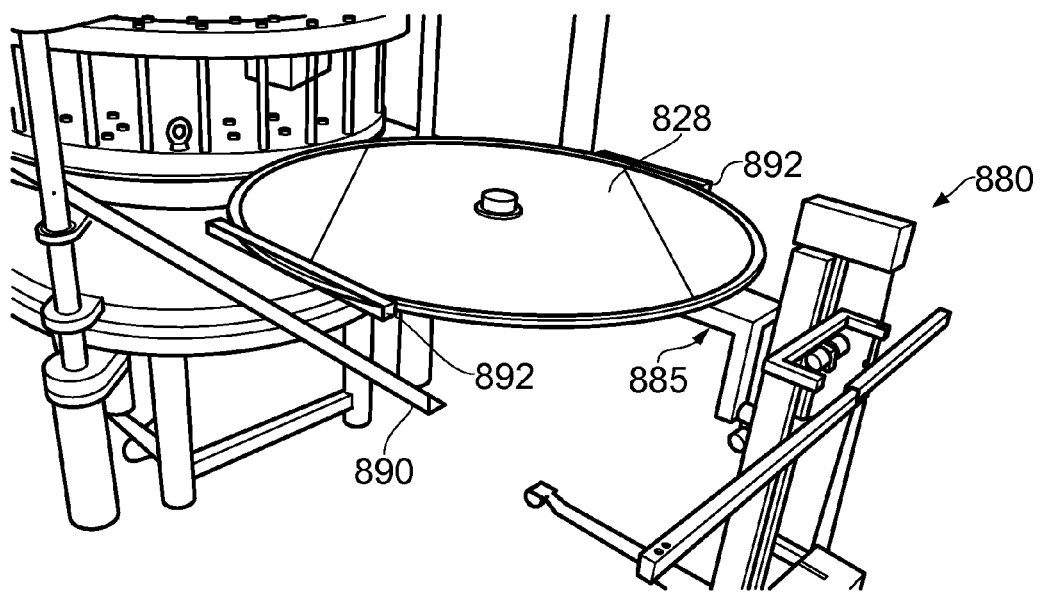
FIG. 9b illustrates removal of the bed support away from the column by the handling device.

The bed support 828 is rolled out from the column a sufficient distance to allow the bed support to become aligned with the central element 886 and support pads 885 x, z (one hidden behind column) on the arms 885 of the handling device 880, FIG. 9a. As shown in FIG. 9b, the arms 885 of the device 880 are then raised until the handling device 880 supports the entire weight of the bed support 828. The rails 890 are detached from the handling device 880 and the bed support is slowly moved orthogonally away from the column. The roller plate 892 can then be detached and the bed support 828 moved to an area where maintenance is to be carried out.

To return to an operational mode, the above procedure is simply reversed. The bed support and/or distributor is returned to the column and affixed to each other and to the backing plate, the nozzle reattached, the adapter assembly lowered and bolted to the column tube.

Access to the bottom bed support and interior of the column will now be described with reference to FIGS. 10 to 17. To access the bottom bed support the bottom nozzle is removed and the tube released from the base assembly by unscrewing the bolts that join it to the base; the tube and upper adapter assembly can then be lifted with the hydraulic cylinders.

Figure 10A:
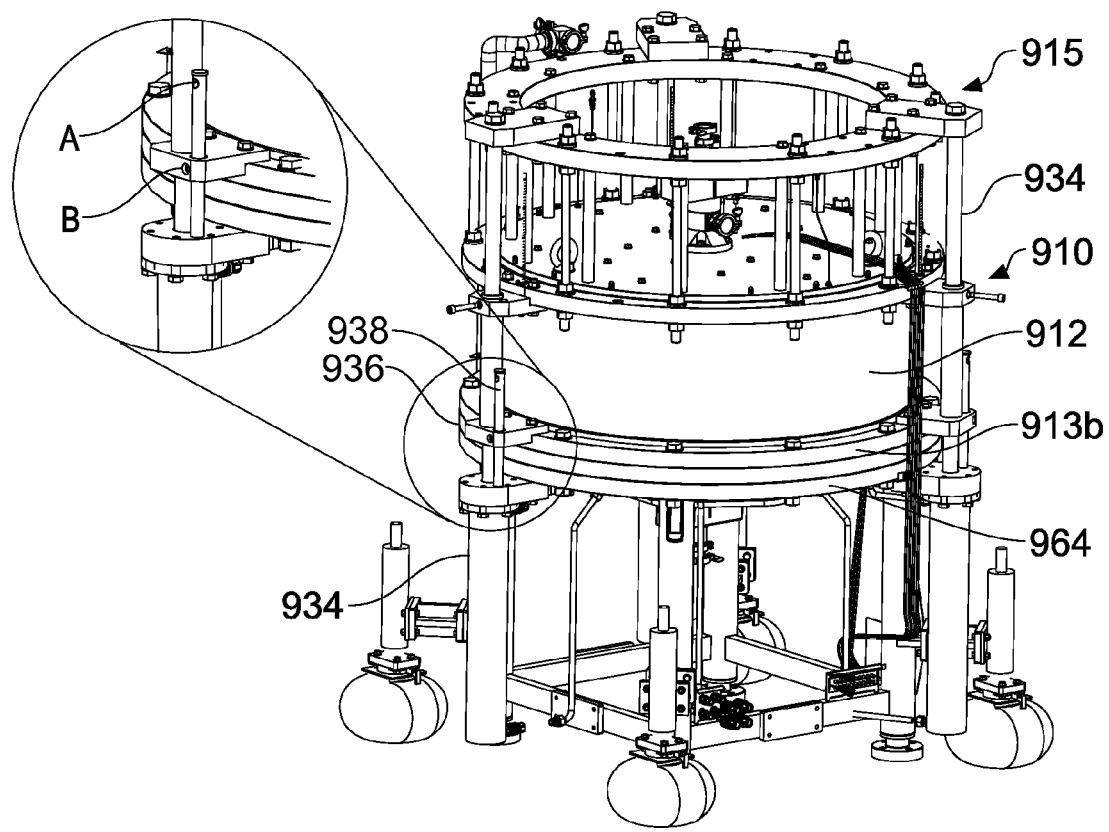
FIG. 10a is a perspective view of a column with an inset showing a locking system in accordance with the invention.
Figure 10B:
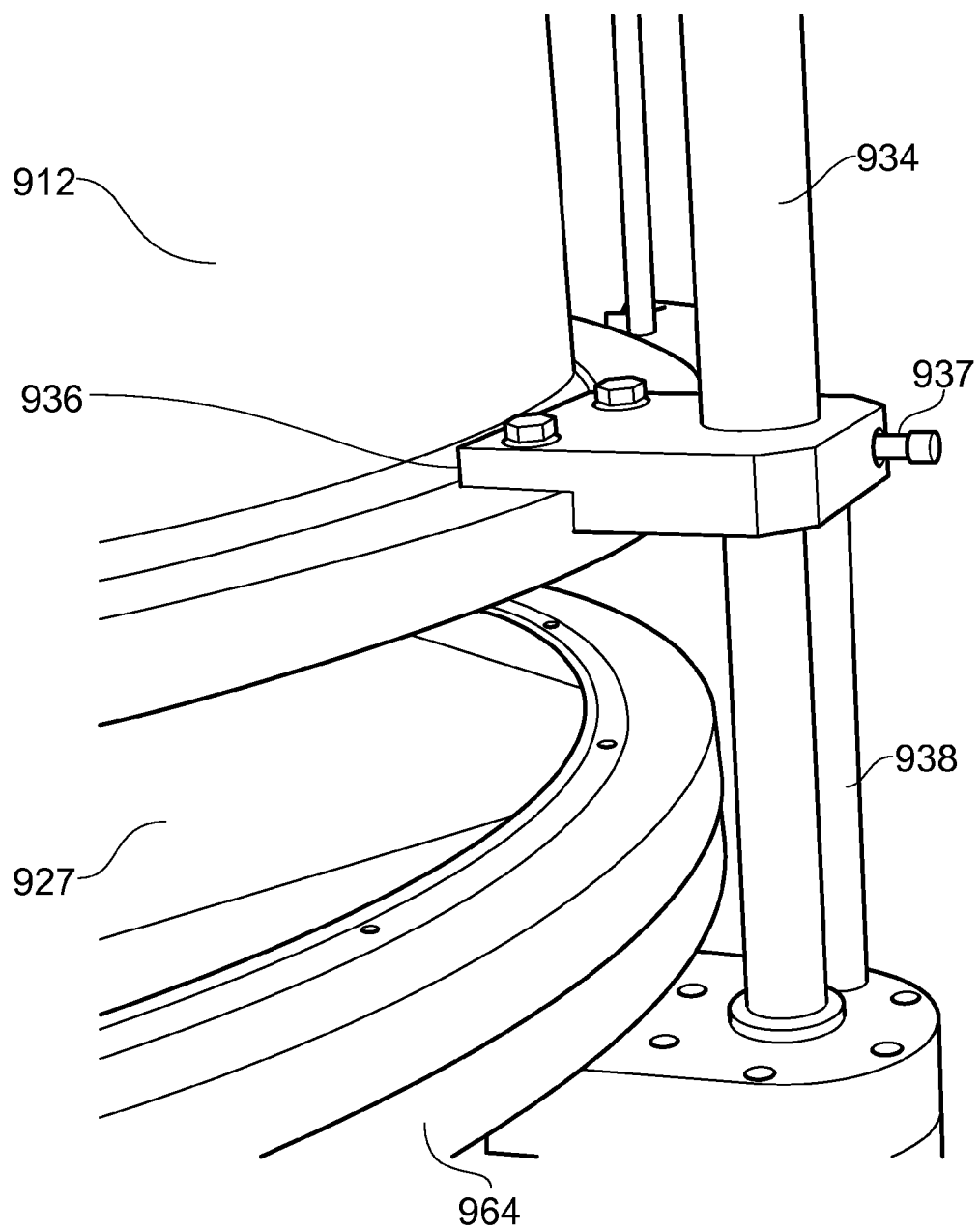
FIG. 10b shows the column tube raised above the base and in the process of being locked into position.

FIG. 10a shows a column 910 as previously described in FIGS. 3 to 5 and FIGS. 7 to 9. The bottom nozzle (see 272 in FIG. 3) is removed by unscrewing the bolts that attach it to the back plate backing plate 964; these bolts are removed from the backing plate side of the base assembly by use of a similar spanner shown in FIG. 5b. The bolts on the lower flange 913b of the column tube which fasten the tube 912 to the bottom backing plate 964 are loosened and unscrewed. The column tube 912 and adapter assembly 915 are lifted by the hydraulic cylinders 934 of the drive system no more than three inches or seventy six millimeters above the base assembly and secured into position by the locking system (see inset of FIG. 10a showing part of the locking system 270 as described previously in FIG. 3 above). Plungers 937 are introduced into the aligned holes in the locking pin 938 and bracket 936 to secure the tube and adapter assembly in position (FIG. 10b). After removal of the bolts securing the tube 912 to the bottom backing plate 964, maintenance can now be carried out on the column in the gap 927 created by raising the tube and adapter assembly. This gap is no more than three inches and typically no more than two inches to restrict operator access to the gap.

Figure 11:
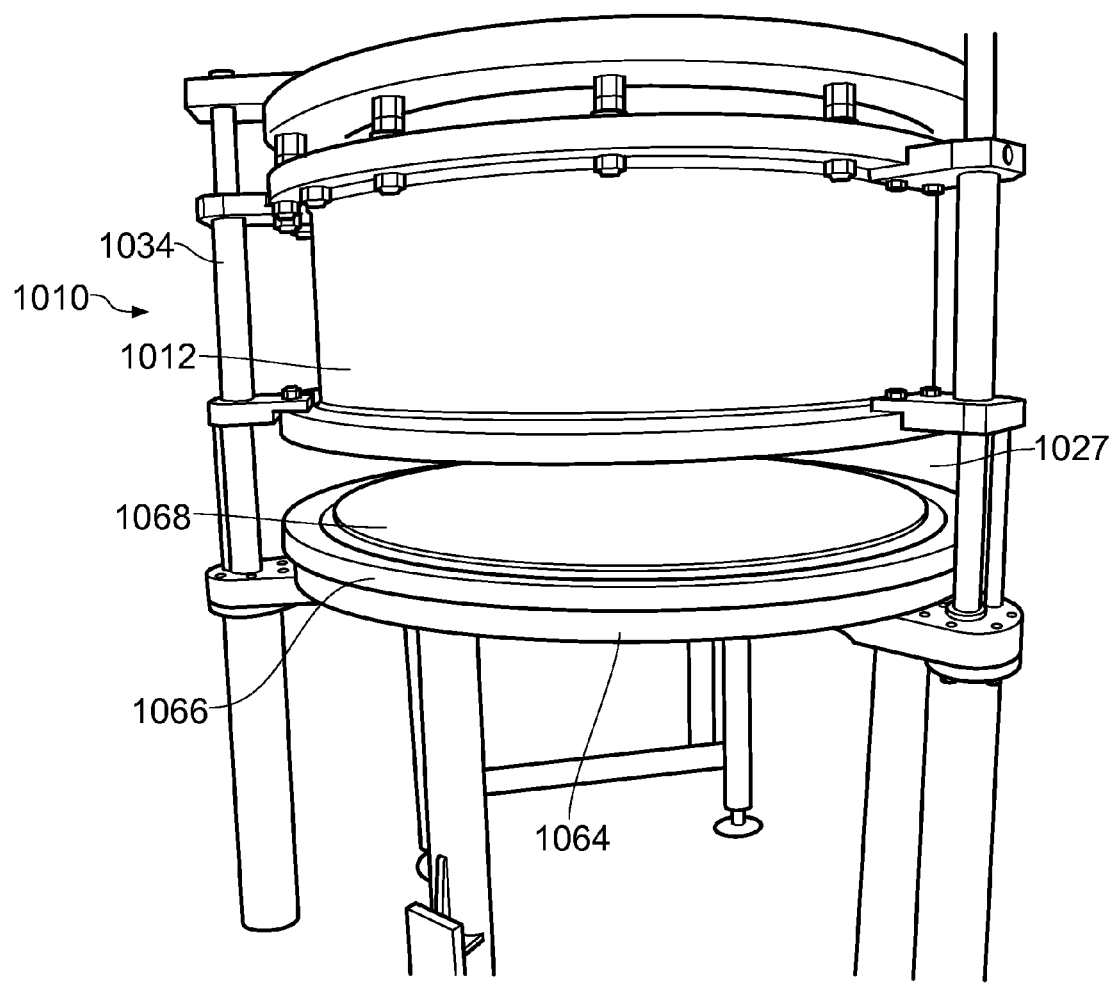
FIG. 11 is a perspective view of a column with the column tube raised and locked into position in readiness for maintenance.

FIG. 11 shows the column 1010 with the tube 1012 raised and mechanically locked to the cylinders 934 in readiness for maintenance. The retaining nut (or fixing means) which fastens the bed support 1068 to the distributor 1066 is released from the backing plate 1064 side of the column 1010. If additional fixing means are present, such as bolts (not shown) which fasten the bed support to the distributor and the backing plate, and are located on the perimeter of the backing plate, these are released from the backing plate face of the column.

Figure 12A:
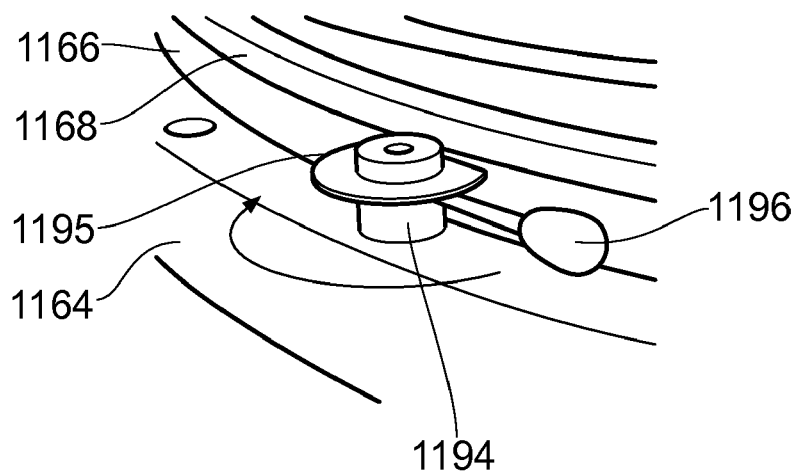
FIGS. 12a, 12b and 12c illustrate the using of a lifting means to lift and separate the bed support from the distributor.
Figure 12B:
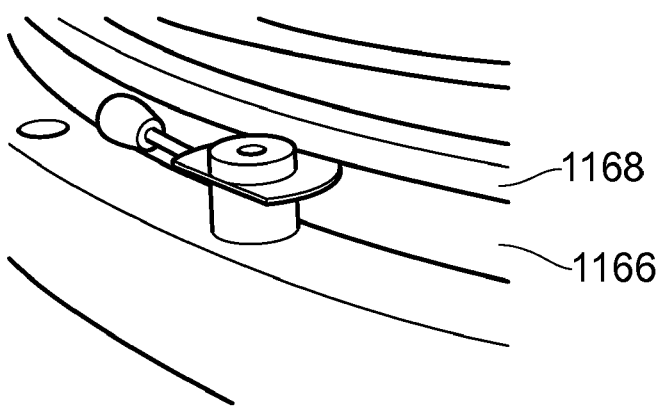
Figure 12C:
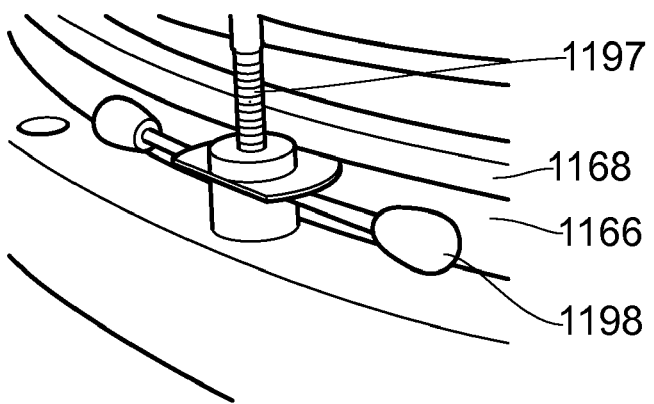
Figure 13:
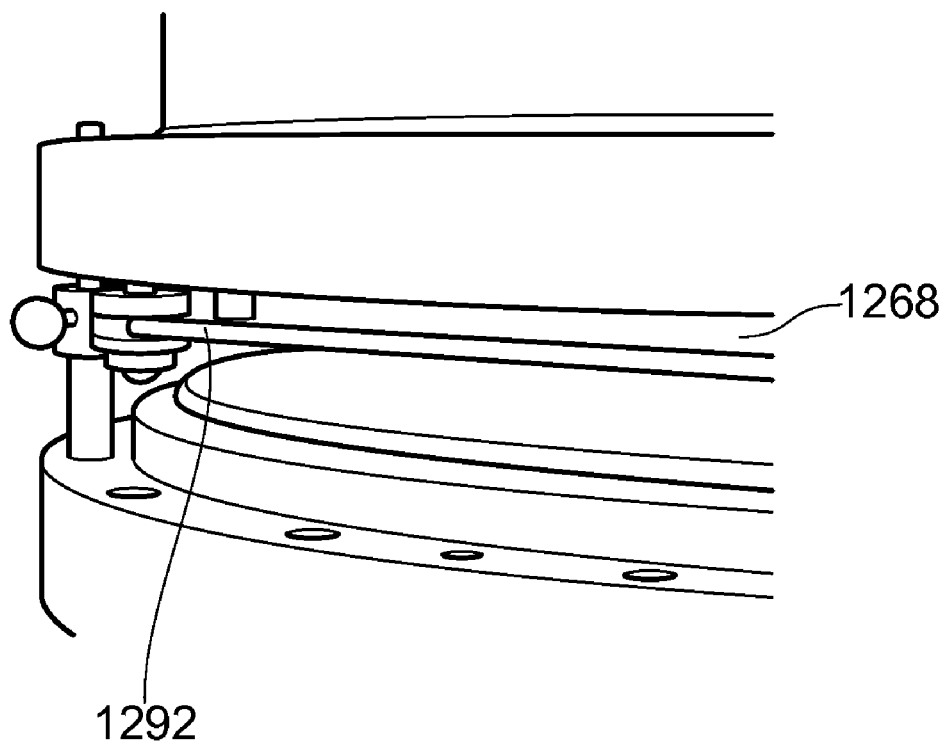
FIG. 13 is a perspective view of the column showing a roller plate attached to the bed support.
Figure 14:
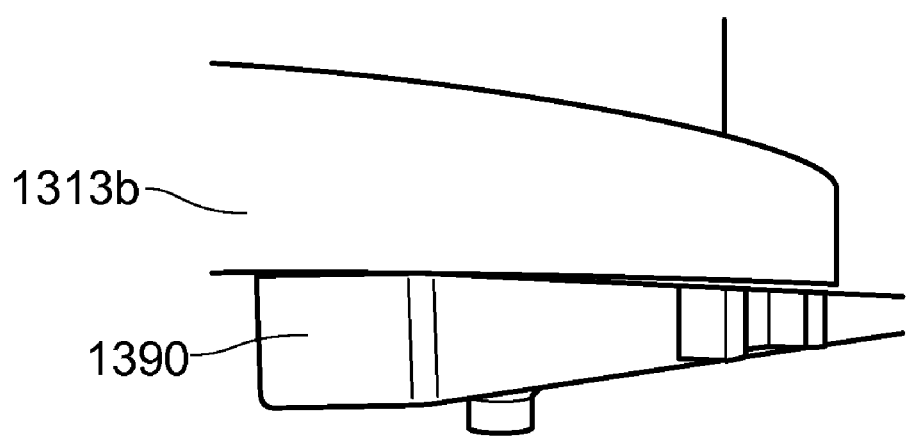
FIG. 14 is a perspective view of the column showing rails attached to the bottom flange.

Before the bottom bed support 1068 can be mounted to the transfer means/roller plates (not shown) and consequently removed from the column 1010, it must be lifted up and away from the distributor 1066. This is accomplished by using lifting means 1194 as shown in FIGS. 12a, 12b and 12c. In one embodiment the lifting means are lifting plates, preferably four lifting plates 1194 which are positioned equidistantly around the rim of the backing plate 1164. Each lifting means 1194 contains a semi-circular cam 1195 which has a beveled edge. When the cam 1195 is positioned as shown in FIG. 12a and then rotated as shown in FIG. 12b with lever 1196 the cam 1195 is inserted between the bed support 1168 and the distributor 1166. By turning the lifting screw 1197 (shown in FIG. 12c), the bed support 1168, which is supported on all four cams 1195, is lifted up a distance sufficient to mount the transfer means or roller plates 1292 at the underside of the bed support's 1268 outer ring (FIG. 13) and to mount the rails 1390 (not shown) to the underside of the tube's bottom flange 1313b (FIG. 14). The opposite end of the rails 1390 can then be affixed to the cross member of the handling device (not shown).

Figure 15:
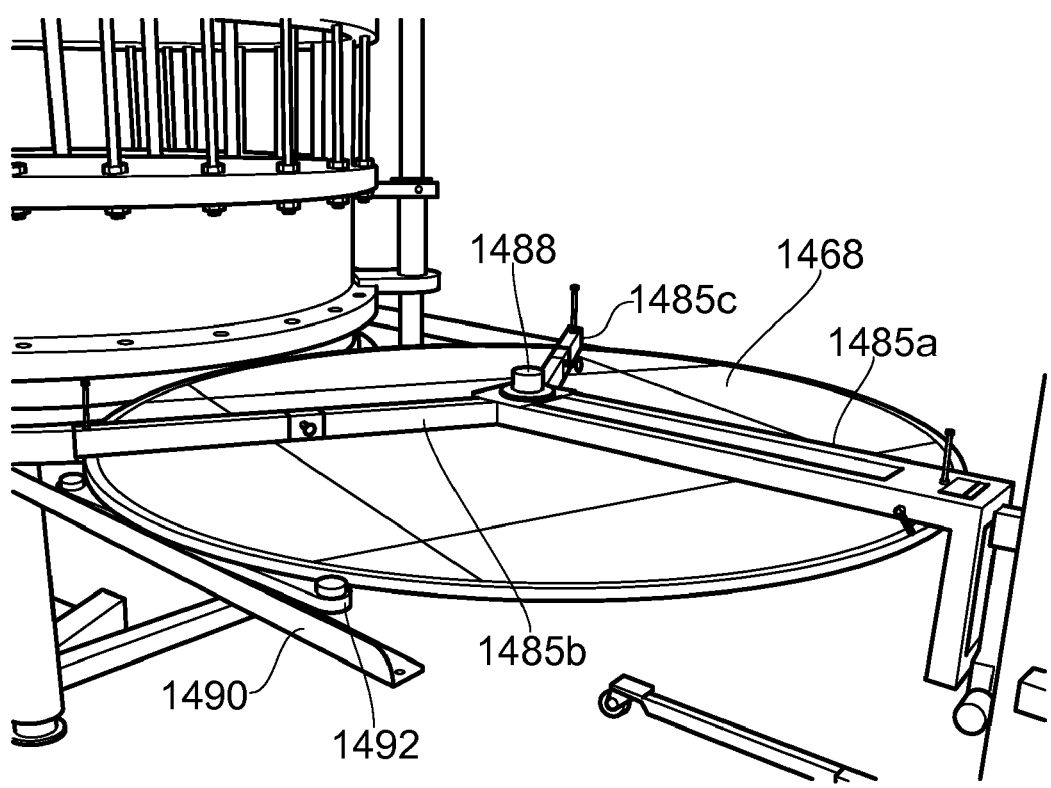
FIG. 15 is a perspective view illustrating the removal of the bottom bed support away from the column by the handling device.

The bed support, with the roller plates mounted to it, is lowered orthogonally to the rails using the lifting screws on all four lifting plates. The lifting screws and the lifting plates are removed (all four can be removed but removing only two is sufficient) and the bed support 1468 is rolled out along the rails 1490 until the threaded central sleeve aligns with the handling device centre element 1488 and the rim threaded holes align with the corresponding holes on the handling device arms 1485 a, b, c, (FIG. 15). The bed support 1468 is affixed to the arms 1485 a, b, c by means of threaded bolts or screws and then lifted above the level of the rails 1490 by the handling device. Following removal of the rails 1490 from the handling device and roller plate 1492, the support 1468 can be moved to a location for maintenance.

Figure 16:
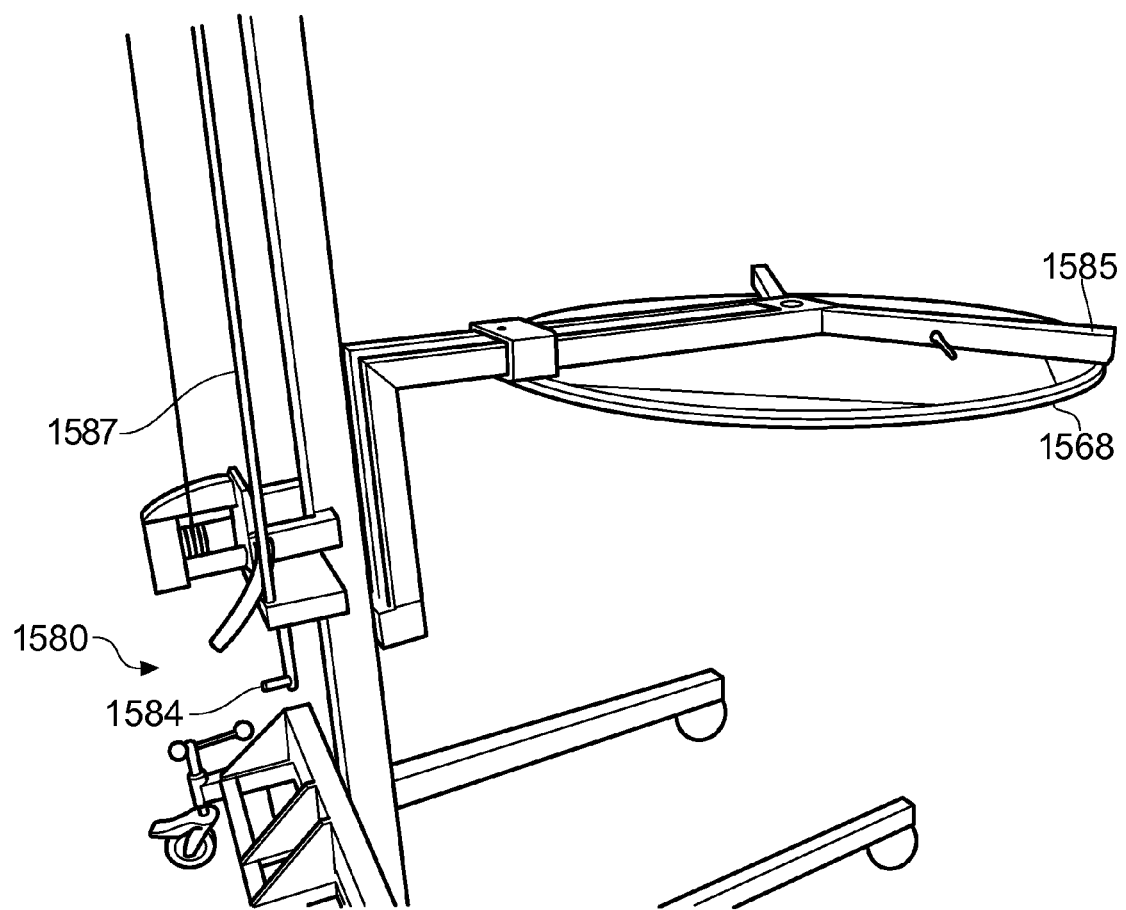
FIG. 16 shows the bed support having been removed from the column in readiness for maintenance.

The bed support can now be cleaned or new O-rings replaced as necessary. Generally the bed support 1568 will be moved away from the column, as shown in FIG. 16, lowered onto a surface (such as a trolley or workbench) and released from the arms 1585 of the handling device 1580 to facilitate cleaning and servicing. The distributor (1066 in FIG. 11) can also be removed and serviced in a similar manner using the lifting device.

Figure 17:
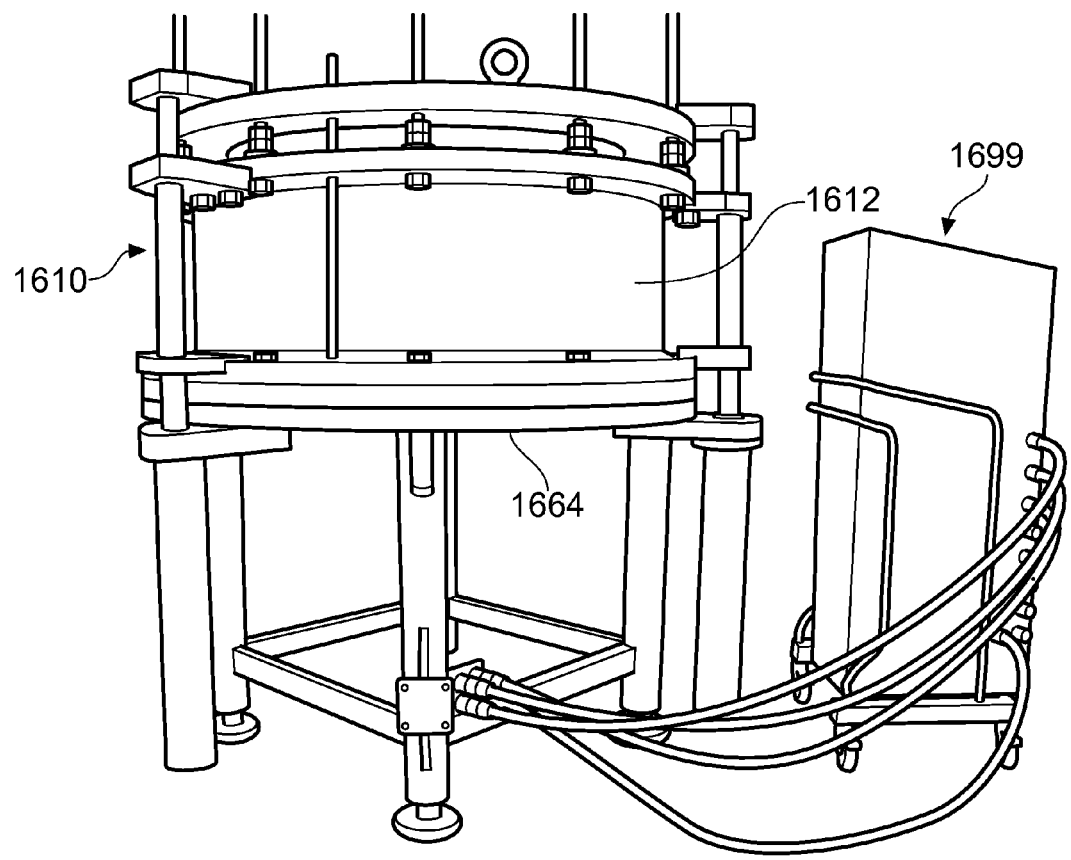
FIG. 17 is a perspective view of the column of FIG. 11 with the column tube lowered awaiting bolting to the base.

Once maintenance or servicing has been completed, the column is returned to an operational mode by simply reversing the process as described above. This involves replacing the bed support/and or distributor in the column, affixing the components to the backing plate, lowering the tube and adapter assembly and reattaching the nozzle. FIG. 17 shows the column 1610 of FIG. 11 connected to the hydraulic control unit 1699 with the tube 1612 lowered and ready to be bolted to the backing plate 1664.

While preferred illustrative embodiments of the present invention are described, one skilled in the art will appreciate that the present invention can be practiced by other than the described embodiments, which are presented for purposes of illustration only and not by way of limitation. The present invention is limited only by the claims that follow.

What is claimed is:

1. A method for conducting maintenance on a chromatography column or parts thereof comprising the steps of:
 a) providing a chromatography column comprising;
  a dispersion system comprising a nozzle including a mobile phase pathway connected to a liquid inlet;
  a tube with an adapter assembly connected to an integrated drive system, said adapter assembly moveable within a cavity of said tube in an operational mode;
  the adapter assembly comprising a backing plate, a distributor and a bed support fastened to each other by releasable fixing means,
  a collection system opposing the dispersion system; and
  one or more seals;
 b) disconnecting the adapter assembly from the tube;
 c) lifting the adapter assembly above the tube with the drive system to provide a gap for access there between;
 d) affixing guide elements to the tube;
 e) unfastening the bed support from the distributor and said backing plate without accessing the interior of the column;
 f) removing the bed support from the column without accessing the interior of the column by means of said guide elements;
 g) conducting maintenance on the column and/or the bed support and/or said one or more seals;
 h) returning the bed support to the column and fastening the bed support and the backing plate to the distributor without accessing the interior of the column;
 i) releasing the guide elements from the tube; and
 j) lowering the adapter assembly to an operational position within the tube and reconnecting the adapter assembly to the tube.

2. The method of claim 1, wherein step c) involves lifting the adapter assembly a distance of no more than three inches or seventy six millimeters above the tube with the drive system to provide a gap for access there between.

3. The method of claim 1, wherein step c) involves lifting the adapter assembly a distance of no more than two inches or fifty millimeters above the tube with the drive system to provide a gap for access there between.

4. The method of claim 1, wherein the guide elements are guide rails.

5. The method of claim 1, wherein step f) and/or step h) additionally comprises using transfer means to move the bed support along the guide elements.

6. The method of claim 5, wherein said transfer means is a roller plate.

7. The method of claim 1, wherein step d) additionally comprises affixing the guide elements to a support.

8. The method of claim 7, wherein said support is a handling device.

9. The method of claim 8, wherein the handling device comprises at least one arm and the method comprises supporting the bed support on or affixing the bed support to said at least one arm of the handling device.

10. The method of claim 1, wherein the drive system is an electric, motorized, hydraulic or pneumatic system.

* * * * *